United States Patent [19]

Kettner et al.

[11] Patent Number: 4,636,492

[45] Date of Patent: Jan. 13, 1987

[54] INHIBITION OF VIRAL PROTEASE ACTIVITY BY PEPTIDE HALOMETHYL KETONES

[75] Inventors: Charles A. Kettner; Bruce D. Korant, both of Wilmington, Del.

[73] Assignee: E. I. Du Pont de Nemours and Company, Wilmington, Del.

[21] Appl. No.: 645,426

[22] Filed: Aug. 29, 1984

[51] Int. Cl.$^4$ .................. A61K 37/02; C07K 5/06; C07K 5/08; C07K 5/10
[52] U.S. Cl. ............................. 514/18; 514/19; 530/330; 530/331; 260/998.2
[58] Field of Search ................ 514/18, 19; 530/330, 530/331; 260/998.2

[56] References Cited
PUBLICATIONS

Lozitskii, et al., *Usp. Sovrem. Biol.* 93:352, (1982).
Korant, *J. Virol.* 10:751, (1972).
Summers et al., *J. Virol.* 10:880, (1972).
Korant et al., *PNAS USA* 76:2992, (1979).
Powers, "Halomethyl Ketone Inhibitors of Proteolytic Enzymes," in Weinstein, ed., *Chemistry and Biochemistry of Amino Acids, Peptides, and Proteins*, (Dekker, New York, 1977), pp. 65–178.
Powers et al., *Biochim. Biophys. Acta* 480:246, (1977).
Ito et al., *Biochem. Biophys. Res. Comm.* 49:343, (1972).
Fittkau et al., *Peptides*, 1982, p. 617, (1983).
Enzyme Systems Products (Product Bulletin, Nov. 1981).

*Primary Examiner*—Delbert R. Phillips

[57] ABSTRACT

Selected tripeptide and tetrapeptide halomethyl ketones are employed in processes for treating viral infection in mammals. These compounds inhibit picornavirus protease activity.

26 Claims, No Drawings

INHIBITION OF VIRAL PROTEASE ACTIVITY BY PEPTIDE HALOMETHYL KETONES

BACKGROUND OF THE INVENTION

This invention relates generally to inhibition of viral proteases, and more particularly, to use of certain peptide halomethyl ketones as specific inhibitors of picornavirus protease activity.

Proteases are enzymes which cleave proteins at specific peptide bonds. In living systems, highly specific proteases and complementary protease inhibitors mediate or control a broad spectrum of biological functions. For example, proteases cleave precursors to form active proteins in post-translational processing of polypeptides, provide mechanisms for zymogen activation cascade reactions such as blood coagulation, fibrinolysis, and certain immunological reactions, and mediate transport of selected proteins across biological membranes. Accordingly, proteases represent potential targets for therapeutic agents designed to function as specific inhibitors of protease activity.

Proteases encoded by viral genomes play a critical role in viral reproduction. Viral proteases cleave large precursor polypeptides produced by infected cells into smaller protein components, or subunits, which are subsequently assembled to form functional virus structures. Lozitskii et al., *Usp. Sovrem. Biol.* 93:352–362 (1982) have reviewed the role of proteolysis in reproduction of avian and mammalian viruses, and have surveyed part of the literature relating to viral protease inhibitors.

Picornaviruses represent a significant class of viral pathogens in humans and other mammals. Included within this class are polioviruses, rhinoviruses, and the viruses which are the etiologic agents of hepatitis A and hoof-and-mouth disease. During picornavirus replication, viral mRNA is translated in a continuous passage of ribosomes along a viral mRNA molecule, producing a linear protein product which is cleaved at selected sites by virus-specified proteases prior to dissociation of a protein/ribosome complex.

A number of workers have sought specific inhibitors of picornavirus protease activity. Korant, *J. Virol.* 10:751–759 (1972), discloses inhibition of poliovirus and echovirus-12 protein processing by chloromethyl ketone derivatives of simple amino acids. Specifically, Korant discloses inhibition by tolylsulfonylphenylalanyl chloromethyl ketone (TPCK) and tolylsulfonyllysyl chloromethyl ketone (TLCK). Summers et al., *J. Virol.* 10:880–884 (1972), similarly disclose inhibition of protease cleavage of large poliovirus-specific polypeptides by TPCK, TLCK, and D- and L-isomers of carbobenzyloxyphenylalanyl chloromethyl ketone (ZPCK). In a subsequent report, Korant et al., *Proc. Natl. Acad. Sci. USA* 76:2992–2995 (1979), describe inhibition of poliovirus protein processing by carbobenzyloxyleucyl chloromethyl ketone (ZLCK).

Various peptide derivatives with capacity to inhibit protease activity are known. Powers, "Haloketone Inhibitors of Proteolytic Enzymes", in *Chemistry and Biochemistry of Amino Acids, Peptides, and Proteins*, Weinstein, ed. (Marcel Dekker, New York, 1977), pp. 65–178, has surveyed the literature reporting inhibition of protease activity by haloketone derivatives of amino acids and peptides. Powers et al., *Biochem. Biophys. Acta* 480:246–261 (1977), disclose inhibition of subtilisin BPN', a bacterial protease, by a series of peptide chloromethyl ketones. Of the compounds tested, acetyl-L-phenylalanyl-L-glycyl-L-alanyl-L-leucyl chloromethyl ketone (Ac-Phe-Gly-Ala-leuCH$_2$Cl) was the fastest inhibitor. A related compound, methoxy-succinyl-L-phenylalanyl-L-glycyl-L-alanyl-L-leucyl chloromethyl ketone (MeOSuc-Phe-Gly-Ala-LeuCH$_2$Cl) is disclosed by Enzyme Systems Products in a November 1981 product bulletin.

Ito et al., *Biochem. Biophys. Res. Commun.* 49:343–349 (1972), describe experiments involving inhibition of chymotrypsin, a digestive protease, by certain peptide aldehydes. Ito et al. also tested for inhibition of chymotrypsin by Ac-Leu-Leu-PheCH$_3$, a tripeptidyl methyl ketone. However, no inhibition was observed at an inhibitor concentration of 600 μg/mL.

Finally, Fittkau et al., "Synthesis and Properties of Peptide Ketones", in *Peptides* 1982, Blaha et al., eds., (de Gruyter, New York, 1983) pp. 617–622, disclose inhibition of thermitase, a thermostable serine protease of *Thermoactinomyces vulgaris*, by certain peptide methyl ketones.

It has now been found that picornavirus protease activity can be inhibited by certain peptide halomethyl ketones. These compounds can potentially be employed in treatment of viral infection in mammals.

SUMMARY OF THE INVENTION

The present invention provides processes for treating picornavirus infection in a mammal, comprising administering to a mammal an effective antiviral amount of a compound of the formula

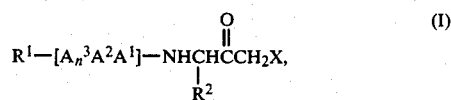

or a physiologically acceptable salt thereof, wherein

A$^1$ is an amino acid residue selected from the group consisting of Ala, Val, Leu, Ile, Phe, Tyr, Gly, Pro, Ser and Thr;

A$^2$ is an amino acid residue selected from the group consisting of Ala, Val, Leu, Ile, and Gly;

A$^3$ is an amino acid residue selected from the group consisting of Ala, Val, Leu, Ile, Phe, Tyr and Gly;

R$^1$ is an N-terminal protecting group; and

R$^2$ is methyl, isopropyl, isobutyl, 4-hydroxybenzyl, or

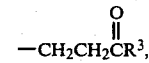

where R$^3$ is amino, methoxyl, ethoxyl, benzyloxy or alkyl of 1 to 6 carbon atoms;

X is Cl or Br; and n is 0 or 1; with the proviso that both A$^3$ and A$^1$ are not simultaneously Ala.

The present invention also provides compounds of the formula

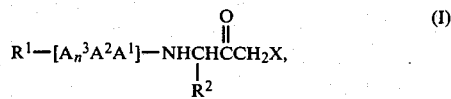

or physiologically acceptable salts thereof, wherein $A^1$, $A^2$, $A^3$, $R^1$, X and n are as defined above, and $R^2$ is $$-CH_2CH_2\overset{O}{\overset{\|}{C}}R^3,$$

where $R^3$ is methoxyl or ethoxyl.

DETAILED DESCRIPTION OF THE INVENTION

The compounds employed in processes of the present invention are halomethyl ketone derivatives of selected tripeptides and tetrapeptides. These compounds inhibit processing of picornavirus capsid proteins by virus-encoded proteases.

As used throughout the specification, the following abbreviations for amino acid residues or amino acids apply:

Ala: L-alanine
Gly: glycine
Gln: L-glutamine
Glu: L-glutamic acid
Leu: L-leucine
Ile: L-isoleucine
Lys: L-lysine
Phe: L-phenylalanine
Pro: L-proline
Ser: L-serine
Thr: L-threonine
Tyr: L-tyrosine
Val: L-valine As used throughout the specification, "N-terminal protecting group" means an arylcarbonyl, alkylcarbonyl, alkoxycarbonyl, aryloxycarbonyl, aralkoxycarbonyl, arylsulfonyl, alkylsulfonyl, or arylsulfonyl peptide protecting group, or other equivalents known to those skilled in the art of peptide synthesis. Gross and Meienhofer, eds., *The Peptides,* Vol. 3, (Academic Press, New York, 1981) pp. 3-81, the disclosure of which is hereby incorporated by reference, describe numerous suitable amine protecting groups. As used herein, either individually or as part of a larger group, "alkyl" means a linear, cyclic, or branched-chain aliphatic moiety of 1 to 10 carbon atoms; "aryl" means an aromatic moiety, e.g., phenyl, of 6 to 18 carbon atoms, unsubstituted or substituted with one or more alkyl, nitro, alkoxy, or halo groups; and "aralkoxy" means an aryl moiety of 7 to 19 carbons having an aliphatic substituent, and, optionally, other substituents such as one or more alkyl, alkoxy, nitro or halo groups. As used herein, "halo" means Cl or Br.

Examples of suitable values for N-terminal protecting group $R^1$ include formyl, acetyl, trifluoroacetyl, benzyloxycarbonyl (carbobenzoxy), substituted benzyloxycarbonyl, tert-butyloxycarbonyl, isopropyloxycarbonyl, allyloxycarbonyl, phthaloyl, benzoyl, acetoacetyl, chloroacetyl, phenoxycarbonyl, methoxysuccinyl, succinyl, 2,4-dinitrophenyl, dansyl, p-methoxybenzenesulfonyl, p-toluenesulfonyl, methanesulfonyl and phenylthio. Particularly convenient values for $R^1$ are carbobenzoxy (Z), tert-butyloxycarbonyl (Boc) and acetyl (Ac).

Certain values for N-terminal protecting group $R^1$ are abbreviated as follows throughout the specification:

Z: Carbobenzoxy
Boc: t-Butyloxycarbonyl
Ac: Acetyl
Et: Ethyl
Suc: Succinyl
MeOSuc: Methoxysuccinyl
DNS: Dansyl
DNP: 2,4-Dinitrophenyl In naming compounds useful in the process of the invention, C-terminal amino acid moiety $$-NHCH\overset{O}{\overset{\|}{C}}-\\ \phantom{-NH}|\\ \phantom{-NHCH}R^2$$

is assigned the name of a corresponding amino acid. Thus, a compound of formula I, above, wherein $R^1$ is Z, $A^1$ is Leu, $A^2$ is Gly, $A^3$ is Phe, $R^2$ is isobutyl, and X is Cl is conventionally named N-carbobenzoxy-L-phenylalanyl-L-glycyl-L-leucyl-L-leucine chloromethyl ketone; this compound is abbreviated herein as Z-Phe-Gly-Leu-LeuCH$_2$Cl.

Contemplated classes of compounds of formula I preferred for use in various embodiments of the invention include the following. A first class includes compounds wherein $R^1$, $R^2$, $A^1$, $A^2$, $A^3$, and X are as previously defined and n is 0. A second class includes compounds wherein $R^1$, $R^2$ and X are previously defined, n is 1, $A^1$ is selected from the group consisting of Phe, Gly, Ala, Pro, Leu, and Ser; $A^2$ is selected from the group consisting of Ala, Val, Leu, Ile, and Gly; and $A^3$ is selected from the group consisting of Ala, Val, Leu, Ile, Phe, Tyr and Gly.

On the basis of superior effectiveness in inhibiting viral replication, those compounds of formula I wherein n is 1; $R^2$ is isobutyl or methoxycarbonylethyl; $R^1$ is Z or MeOSuc; $A^1$ is Ala, Gly or Leu; $A^2$ is Ile or Gly; and $A^3$ is Phe, Ala or Leu are particularly preferred for use in the processes of the present invention.

The compounds of the present invention are compounds of the foregoing formula I wherein $R^2$ is methoxycarbonylethyl or ethoxycarbonylethyl. Contemplated classes of compounds within this genus include classes corresponding in scope to those previously defined for the compounds employed in the processes of the invention. Preferred compounds of the invention are those wherein n is 1; $R^1$ is Z or MeOSuc; $R^2$ is methoxycarbonylethyl; $A^1$ is Ala or Leu; $A^2$ is Gly; and $A^3$ is Phe or Ala. Particularly preferred compounds are those wherein $A^1$ is Leu; $A^3$ is Phe; and $R^1$ is MeOSuc.

Specific examples of compounds useful in various embodiments of the invention include Z-Phe-Gly-Leu-LeuCH$_2$Cl;
Z-Phe-Gly-Ala-LeuCH$_2$Cl;
Ac-Phe-Gly-Ala LeuCH$_2$Cl;
Suc-Phe-Gly-Ala-LeuCH$_2$Cl;
MeOSuc-Phe-Gly-Ala-LeuCH$_2$Cl;
DNS-Phe-Gly-Ala-LeuCH$_2$Cl;
DNP-Phe-Gly-Ala-LeuCH$_2$Cl;
Boc-Gly-Ala-LeuCH$_2$Cl;
Z-Leu-Gly-Ala-LeuCH$_2$Cl;

Z-Phe-Gly-Gly-LeuCH$_2$Cl;
Z-Phe-Leu-Ala-LeuCH$_2$Cl;
Z-Phe-Gly-Phe-LeuCH$_2$Cl;
Z-Phe-Gly-Ser-LeuCH$_2$Cl;
Z-Phe-Gly-Pro-LeuCH$_2$Cl;
Z-Phe-Gly-Ala-LeuCH$_2$Br;
MeOSuc-Ala-Ile-Phe-LeuCH$_2$Cl;
MeOSuc-Phe-Gly-Leu-Glu(OCH$_3$)CH$_2$Cl;
MeOSuc-Ala-Ile-Phe-Glu(OCH$_3$)CH$_2$Cl;
Z-Phe-Gly-Ala-ValCH$_2$Cl; and
Z-Phe-Gly-Ala-TyrCH$_2$Cl.

Physiologically acceptable salts of compounds of formula I include acid addition salts of free base, if present, wherein the acid can be organic or inorganic, e.g., hydrochloric, phosphoric, maleic, acetic, citric, succinic, etc. Alternatively, salts of free peptidic acids, including sodium, potassium, and ammonium salts, are included within the scope of compounds useful in the present invention.

In practicing the process of the invention, the foregoing compounds can be employed alone, in combination with one another, in combination with other therapeutic agents, or in combination with various inert pharmaceutically acceptable carriers in a variety of dosage forms, orally or parenterally. Dose requirements will vary with the compound and dosage form employed and the animal being treated. Typically, therapy is initiated at lower dosages and dosage is increased until the desired inhibiting effect is achieved.

The compounds employed in the invention can be prepared by techniques generally corresponding to those disclosed by Kettner et al., [Arch. Biochem. Biophys. 162:56 (974).

First, N-protected peptides or amino acids are reacted with about one equivalent of N-methylmorpholine and one equivalent of isobutyl chloroformate at about −20° C., generating a mixed peptide-isobutyric acid anhydride. This standard technique is described by Anderson et al., *J. Amer. Chem. Soc.*, 89:5012 (1967). Second, the resulting mixed anhydride is treated with about one equivalent of diazomethane in tetrahydrofuran or other suitable inert, aprotic solvent at 0° C., generating an N-protected peptide or amino acid diazomethyl ketone. Third, the latter compound is treated with a solution of HCl or HBr in anhydrous ethanol or ether at 0° C., producing an N-protected halomethyl ketone.

Larger peptide halomethyl ketones can be assembled by repetitively coupling a deprotected halomethyl ketone to mixed anhydrides of other N-protected peptides or amino acids generated according to the foregoing procedure. Deprotection of N-terminal amino groups can be accomplished by treatment with trifluoroacetic acid, anhydrous HF, anhydrous HCl, or by other methods known to those skilled in the art.

Procedures suitable for producing specific compounds employed in processes within the scope of the present invention are described in paragraphs preceding the Examples set forth below. In the preparative procedures and Examples, all parts and percentages are by weight, and all degrees are Celsius, unless otherwise noted.

GENERAL SYNTHETIC PROCEDURES

1. Mixed Anhydride Coupling Procedure

Approximately 1 g of an N-protected amino acid or peptide is dissolved in 20 mL of tetrahydrofuran (THF), and the resulting solution is cooled to −20°. N-methylmorpholine (1 eq) and isobutyl chloroformate (1 eq) are added and after 5 minutes, an additional 10 mL of cold THF and an equivalent of triethylamine are added. The resulting mixture is immediately added to an equivalent of an amine hydrochloride or trifluoroacetate dissolved in 5 mL of dimethylformamide (DMF). The ensuing reaction is allowed to stir 1 hour at −20° and then 2 hours at about 23°. The resulting mixture is filtered and the filtrate thereby obtained is then concentrated to approximately 5 mL by evaporation. The resulting concentrate or residue is dissolved in ethyl acetate and washed sequentially with 0.2N-hydrochloric acid, 5% sodium bicarbonate solution, and saturated aqueous sodium chloride. The resulting organic solution is then dried briefly over sodium sulfate, filtered, and finally evaporated to leave a crude peptide product.

2. N-Hydroxysuccinimide (OSu) Coupling Procedure

N-hydroxysuccinimide esters of N-protected amino acids and peptides can be prepared by procedures substantially similar to those disclosed by Anderson et al., *J. Am. Chem. Soc.*, 86:1839 (1964). An OSu ester is dissolved in a minimial volume of dioxane, and the resulting solution is added to an equal volume of an aqueous solution consisting of 1.5 eq of triethylamine and either 1.5 eq of an amino acid or 1.1 eq of a peptide, forming a reaction mixture. After about 5 minutes, if a complete solution is not obtained, a small test sample of the reaction mixture can be diluted with water and another sample diluted with dioxane. On the basis of the results obtained, the reaction mixture is then diluted with the indicated solvent (either water or dioxane) until completely dissolved. After the reaction has proceeded to completion, the reaction mixture is acidified with hydrochloric acid and the resulting product extracted into ethyl acetate. The resulting extract is then washed with 0.2N hydrochloric acid followed by 0.2N hydrochloric acid in saturated sodium chloride. The washed extract is then dried over sodium sulfate, filtered, and finally evaporated to dryness to leave a crude peptide.

3. Other Coupling Procedures

Dansyl, 2,4-dinitrophenyl, and methoxysuccinyl derivatives of peptides are prepared by reacting a selected chloride, fluoride, or N-hydroxysuccinimide ester with an appropriate peptide. Acetyl and succinyl derivatives can be prepared from the corresponding anhydrides. A peptide hydrochloride or trifluoroacetate salt is dissolved in 50% aqueous dioxane at a level of 0.25 mmol/mL and the resulting solution is cooled to 0°. A selected coupling agent (1.0–1.2 eq) is dissolved in dioxane and added along with 2 eq of sodium bicarbonate. The resulting reaction is monitored by following the disappearance of ninhydrin positive material.

4. Saponification of Methyl Esters

An N-protected methyl ester is dissolved in dioxane (1 mL/mmole), and an equal volume of 1.00N sodium hydroxide is added over a period of 30 minutes. Disappearance of starting material is monitored by thin-layer chromatography. After the resulting reaction has proceeded to completion, an equivalent of 1.00N hydrochloric acid is added, and the solution is diluted to 100 mL with water. The product is then extracted into ethyl acetate, and the resulting organic phase washed with 0.2N hydrochloric acid followed by 0.2N hydrochloric acid in saturated sodium chloride. Solvent is then removed by evaporation to leave a crude carboxylic acid.

5. Hydrolysis of the Boc Group

Boc protecting groups are removed from peptides by dissolving a selected peptide in trifluoroacetic acid and stirring the soution for 5 minutes at room temperature. Cold ether is then added. If a precipitate is obtained upon addition of ether, it is triturated with ether and isolated. If no precipitate is obtained, the ether is evaporated and toluene is added to precipitate deprotected peptide as a trifluoroacetic acid salt.

Alternatively, a Boc-protected peptide can be dissolved in ethanolic hydrochloric acid (2.0–3.5N) and the resulting solution stirred at about 23° for about 30 minutes, followed by evaporation of solvent. In all cases, peptide hydrochloride or trifluoroacetate salts are dried overnight under vacuum in the presence of solid potassium hydroxide and phosphorus pentoxide.

6. Hydrolysis of t-Butyl Esters (Bu)

t-Butyl peptide esters are dissolved in trifluoroacetic acid, and the resulting solution is stirred for 1 hour at room temperature. Solvent is then evaporated, the resulting residue is redissolved in toluene. Following a second toluene evaporation step, the remaining residue is dried under vacuum with solid potassium hydroxide. Crude product is crystallized from an appropriate solvent, e.g., toluene or ethyl acetate.

7. Thin Layer Chromatography (TLC) Procedures

TLCs are run on 5×10 cm silica gel plates, using a fluorescent indicator. Spots are visualized by conventional techniques, using either a UV light or an iodine jar. Peptides having free amino groups protected by Boc groups are exposed to HCl vapors, and then stained with ninhydrin. The following solvent systems are useful for chromatography:

methanol:chloroform (1:9)
butanol:acetic acid:water (4:1:1)
ethyl acetate:hexane (8:2)

SYNTHESIS OF PEPTIDE HALOMETHYL KETONES

Representative peptide halomethyl ketones were prepared by the indicated literature procedure or as described below:

A. Ac-Phe-Gly-Ala-LeuCH$_2$CL

Ac-Phe-Gly-Ala-LeuCH$_2$Cl was prepared by condensation of N-acetyl-L-phenylalanylglycyl-L-alanine with leucine chloromethyl ketone hydrochloride using a mixed anhydride procedure employing isobutyl chloroformate, Powers et al., *Biochem. Biophys. Acta.* 480:246–261 (1977), describes an analogous procedure. Crude product was recrystallized from ethyl acetate to provide a white crystalline solid, m.p. 152.4°–153.8° (reported m.p. 167°–168°).

B. Z-Phe-Gly-Ala-LeuCH$_2$Cl

A solution of 4.00 g (9.4 mmol) of Z-Phe-Gly-Ala-OH and 0.95 g of N-methylmorpholine in 100 mL of THF was cooled to −20° under nitrogen, and then 1.28 g of isobutyl chloroformate was added. After 5 minutes a solution of 1.14 g of leucine chloromethyl ketone hydrochloride in dry acetone was added, followed by 0.95 g of N-methylmorpholine. The resulting reaction mixture was stirred and allowed to warm to about 25° over a period of 2 hours. Solvent was evaporated, and the resulting residue was dissolved in ethyl acetate. This solution was washed with ice water, followed by cold 5% citric acid. The resulting solution was dried and then solvent was evaporated to leave 5.63 g of a frothy solid. This material was triturated overnight with 250 mL of ether. The resulting gel-like product was filtered from the ether and washed with additional ether, providing 3.10 g of crude product as a fine white powder. A 2.56 g portion was dissolved in 25 mL of warm ethyl acetate, forming a cloudy solution. This solution was filtered through carbon (Celite) and an additional 200 mL of ether was added. After seeding, 1.15 g of fine needle-like crystals of Z-Phe-Gly-Ala-LeuCH$_2$Cl precipitated and were collected. These crystals melted at 138°–141.8°; $\delta_D^{25}$ −59° (C=0.45 g/100 mL in acetone).

Anal: Calcd. for C$_{29}$H$_{37}$ClN$_4$O$_6$: C, 60.78; H, 6.51; N, 9.78; Found: C, 60.45; H, 6.44; N, 9.69.

C. Z-Phe-Gly-Leu-LeuCH$_2$Cl

As a preliminary step in synthesis of the foregoing compound, Z-Phe-Gly-Leu-OH was prepared by the following procedure.

The N-hydroxysuccinimide ester of Z-Phe-OH (19.15 g, 48.3 mmol) was dissolved in 50 mL of dioxane and the resulting solution was filtered into a solution consisting of H-Gly-Leu-OH (10.0 g, 53.1 mmol), triethylamine (10.1 mL, 72.4 mmol), and water (50 mL). This reaction mixture was stirred overnight at about 23°, and then concentrated approximately 60% by evaporation. The resulting concentrated solution was diluted with 1.0N hydrochloric acid until acidic. Product Z-Phe-Gly-Leu-OH was extracted into ethyl acetate, and the resulting extract was washed with 0.2N hydrochloric acid, followed by saturated aqueous sodium chloride adjusted to 0.10N hydrochloric acid. After washing, the ethyl acetate solution was dried over anhydrous sodium sulfate and filtered. The ethyl acetate was then evaporated to yield 22.5 g of a white, foamy product, which was subsequently crystallized from ethyl acetate to yield 16.7 g of Z-Phe-Gly-Leu-OH (m.p. 147°–148°).

Anal: Calcd. for C$_{25}$H$_{31}$N$_3$O$_6$: C, 63.94; H, 6.67; N, 8.95; Found: C, 64.19; H, 6.65; N, 8.90.

H-LeuCH$_2$Cl.HCl was prepared substantially according to the procedure disclosed by Kettner et al., *Arch. Biochem. Biophys.* 165:739–743 (1974).

A mixed anhydride was prepared by dissolving Z-Phe-Gly-Leu-OH (1.05 g, 2.24 mmol) in 10 mL of tetrahydrofuran, cooling the resulting solution to −20°, adding N-methylmorpholine (0.25 mL, 2.24 mmol) and isobutyl chloroformate (0.29 mL, 2.24 mmol). The resulting mixture was stirred for 5 minutes at −20°, and then 20 mL of cold tetrahydrofuran and triethylamine (0.31 mL, 2.24 mmol) were added. This mixture was added to a solution of H-LeuCH$_2$Cl.HCl (0.48 g, 2.24 mmol) in 5 mL cold N,N-dimethylformamide. The resulting reaction mixture was stirred for about 1 hour at −20°, and then for 2 hours at about 23°. The mixture was then filtered, and tetrahydrofuran evaporated from the filtrate. The resulting residue was dissolved in 100 mL of ethyl acetate. This solution was then sequentially washed with 0.2N hydrochloric acid, 5% aqueous sodium bicarbonate, and saturated aqueous sodium chloride. The washed extract was then dried over anhydrous sodium sulfate and then solvent was evaporated to yield 1.2 g of a foam. This product was crystallized from ethyl acetate to yield 0.94 g (m.p. 160°-161.5°) of Z-Phe-Gly-Leu-LeuCH$_2$Cl.

Anal: Calcd. for C$_{32}$H$_{43}$N$_4$O$_6$Cl: C, 62.47; H, 7.06; N, 9.11; Found: C, 62.32; H, 6.90; N, 9.14.

D Z-Phe-Gly-Ala-LeuCH$_2$Br

A mixed anhydride of Z-Phe-Gly-ALa-OH (0.41 g, 0.95 mmol) was prepared and coupled to H-LeuCH$_2$Br.HBr substantially according to the procedure described for preparation of Z-Phe-Gly-Leu-CH$_2$Cl, above. The resulting product was crystallized from ethyl acetate:hexane to yield 0.30 g. Product was recrystallized from the same solvents to yield 0.07 g, m.p. 135.5°-138° (dec.).

Anal: Calcd. for C$_{29}$H$_{37}$N$_4$O$_6$Br: C, 56.39; H, 6.05; N, 9.07; Found: C, 56.70; H, 6.26; N, 8.97.

E. Z-Phe-Gly-Ala-ValCH$_2$Cl

First, precursor H-ValCH$_2$Cl.HCl was prepared by dissolving Boc-Val-OH (6.5 g, 30 mmol) in 10 mL of THF and treating it with N-methylmorpholine (3.3 mL, 30 mmol) and isobutyl chloroformate (3.9 mL, 30 mmol) for 10 minutes at −20°. The resulting mixture was filtered and the retained material was washed with 40 mL of cold THF. The combined filtrates were added to 200 mL of diazomethane:ether. The resulting solution was stirred for 2 hours at 0°, and then solvent was removed by evaporation to yield an oil. The oil was dissolved in ethyl acetate, washed with 5% sodium bicarbonate followed by saturated aqueous sodium chloride, and then dried over sodium sulfate. Evaporation of solvent left 6.4 g of an oil. The oil was dissolved in 100 mL of ether, and the resulting solution was treated with a 5% excess of ethanolic HCl for 15 minutes at 0°. This solution was washed with cold water followed by saturated aqueous sodium chloride, and then dried over sodium sulfate. After evaporation of solvent, product was washed with hexane to yield 2.7 g of Boc-ValCH$_2$Cl (m.p. 70°-73°). Boc-ValCH$_2$Cl (1.0 g) was deblocked by stirring with 5 mL of 3N ethanolic HCl for 30 minutes at about 23°. Solvent was evaporated and the resulting residue was triturated with ether to yield 0.69 g of H-ValCH$_2$Cl.HCl.

Z-Phe-Gly-Ala-OH (1.60 g, 3.73 mmol) was then coupled to H-ValCH$_2$Cl.HCl by a procedure substantially similar to that described for the preparation of Z-Phe-Gly-Leu-LeuCH$_2$Cl, above. The resulting product was crystallized from ethyl acetate:ether to yield 1.29 g of Z-Phe-Gly-Ala-ValCH$_2$Cl (m.p. 143°-144°).

Anal. Calcd. for C$_{28}$H$_{35}$N$_4$O$_6$Cl: C, 60.14; H, 6.32; N, 10.02; Found: C, 59.92; H, 6.25; N, 10.05.

F. Z-Phe-Gly-Ala-TyrCH$_2$Cl

Boc-TyrCHN$_2$ was prepared by dissolving Boc-Tyr-OH (10 g, 35.5 mmol) in 30 mL of tetrahydrofuran and then reacting it with N-methylmorpholine (3.91 mL, 35.5 mmol) and isobutyl chloroformate (4.62 mL, 35.5 mmol) for 5 minutes at −20°. The resulting reaction mixture was filtered, and the material retained by the filter was washed with 50 mL of cold tetrahydrofuran. The resulting filtrates were collected and combined. The combined filtrates were added to 150 mL of diazomethane:ether (∼40 mmol) and the resulting reaction mixture was stirred for 15 minutes at 0°. Solvent was then evaporated with a stream of nitrogen. The remaining residue was dissolved in ethyl acetate and the resulting solution was washed with water followed by saturated aqueous sodium chloride. The washed solution was then dried over sodium sulfate, and then solvent was evaporated to yield a crude product. This material was chromatographed on a 4 cm column containing 75 g of silica gel, using chloroform as a solvent, to yield 3.67 g of Boc-TyrCHN$_2$. This product crystallized from ether to yield 1.86 g (m.p. 136°-137°) in a first crop, and 0.58 g (m.p. 133.5°-134.5°) in a second crop. NMR in CDCl$_3$ indicated a diazo proton at δ 5.27.

Anal: Calcd. for C$_{15}$H$_{19}$N$_3$O$_4$: C, 58.99; H, 6.28; N, 13.76; Found: C, 59.08; H, 6.16; N, 13.65.

Boc-TyrCHN$_2$ (1.81 g, 5.92 mmol) was dissolved in 30 mL of tetrahydrofuran, and the resulting solution wwas treated with 3.45N ethanolic:HCl (1.72 mL, 5.92 mmol) for 5 minutes at 0°. Solvent was removed by evaporation on a rotary evaporator without temperature regulation. The remaining residue was dissolved in ethyl acetate, and the resulting solution was washed with 0.2N hydrochloric acid followed by saturated aqueous sodium chloride. The washed solution was dried over sodium sulfate, and then solvent was evaporated to yield crystalline Boc-TyrCH$_2$Cl. Crystals were isolated and washed with cold ether to yield 0.45 g (m.p. 110°-112°) in a first crop, and 0.90 g (m.p. 110°-112°) in a second crop. NMR spectra in CDCl$_3$ corresponded to that expected, except that methylene protons of —COCH$_2$Cl appears as a doublet at δ4.1.

Anal: Calcd. for C$_{15}$H$_{20}$NO$_4$Cl: C, 57.41, H, 6.44; N, 4.46; Found: C, 57.66; H, 6.66; N, 4.52.

Boc-TyrCH$_2$Cl (0.5 g) was deblocked by treatment with 20 mL of 3.5N ethanolic HCl for 30 minutes at about 23°. Solvent was evaporated and the resulting product, H-TyrCH$_2$Cl.HCl (0.45 g), was dried in vacuo over solid potassium hydroxide and phosphorus pentoxide.

Z-Phe-Gly-Ala-OH (0.77 g, 1.80 mmol) was coupled to H-TyrCH$_2$Cl.HCl by a mixed anhydride coupling procedure substantially similar to that described for preparation of Z-Phe-Gly-Leu-LeuCH$_2$Cl in Procedure E, above. Product was crystallized from ethyl acetate to yield 0.73 g of Z-Phe-Gly-Ala-TyrCH$_2$Cl. Product slowly decomposed at 140°-160° and melted with complete decomposition at 160°-160.5°.

Anal: Calcd. for C$_{32}$H$_{35}$N$_4$O$_7$Cl: C, 61.67; H, 5.67; N, 8.99; Found: C, 61.60; H, 5.92; N, 8.69.

G. MeOSuc-Phe-Gly-Leu-LeuCH$_2$Cl

MeOSuc-Phe-Gly-Leu-OH was prepared from Z-Phe-Gly-Leu-OH, as described above in Procedure C. Z-Phe-Gly-Leu-OH (4.00 g, 8.52 mmol) was dissolved in 100 mL of methanol and hydrogenated in the presence of 1.0 eq of anhydrous HCl and 0.50 g of 10% Pd on carbon overnight in a Parr apparatus. The resulting reaction mixture was filtered and solvent was evaporated to yield 3.1 g of H-Phe-Gly-Leu-OH as a foam.

This product was dissolved in 5 mL of N,N-dimethylformamide, to which N-hydroxysuccinimide ester of methoxysuccinic acid (1.9 g, 8.4 mmol) and triethylamine (1.2 mL, 8.4 mmol) were added. This reaction mixture was stirred for 0.50 hr at ambient temperature, then additional triethylamine (0.58 mL, 4.2 mmol) was added. The reaction mixture was then stirred overnight. At this point, 5 mL of a 5% solution of aqueous sodium bicarbonate was added. After 5 min, the reaction mixture was diluted to 50 mL with 5% aqueous sodium bicarbonate to yield a precipitate, which was discarded. Ethyl acetate was added to the reaction mixture to extract product MeOSuc-Phe-Gly-Leu-OH. The aqueous portion of the resulting extraction mixture was acidified with hydrochloric acid, and then the ethyl acetate phase or extract was separated from the aqueous portion. The extract was washed with 0.20N hydrochloric acid, followed by saturated sodium chloride prepared in 0.20N hydrochloric acid. The washed solution was then dried over sodium sulfate. Solvent was evaporated and the resulting residue was crystallized from ethyl acetate, yielding 1.30 g of MeOSuc-Phe-Gly-Leu-OH (m.p. 167.5°–168.5°).

Anal: Calcd. for $C_{23}H_{32}N_3O_7$: C, 58.91; H, 6.76; N, 9.37; Found: C, 59.20; H, 6.99; N, 9.06.

MeOSuc-Phe-Gly-Leu-OH (1.0 g, 2.23 mmol) was coupled to H-LeuCH$_2$Cl HCl by a procedure substantially similar to that described for preparation of Z-Phe-Gly-Leu-LeuCH$_2$Cl. After coupling, solvent was evaporated to yield a foamy product which crystallized from ethyl acetate, providing 0.30 g (m.p. 116°–117°) of MeOSuc-Phe-Gly-Leu-LeuCH$_2$Cl in a first crop and 0.25 g (m.p. 115°–116°) in a second crop. A sample of the first crop was analyzed.

Anal: Calcd. for $C_{29}H_{43}N_4O_7Cl$: C, 58.51; H, 7.30; N, 9.42; Found: C, 58.67; H, 7.20; N, 9.31.

H. Suc-Phe-Gly-Ala-LeuCH$_2$Cl

Boc-Phe-Gly-Ala-OH was prepared substantially according to the mixed anhydride coupling procedure described previously, except amine components were added in tetrahydrofuran or tetrahydrofuran containing the minimum quantity of water needed to dissolve the amine hydrochlorides. Methyl esters were saponified with aqueous sodium hydroxide in methanol.

Boc-Gly-Ala-OCH$_3$ was prepared by coupling Boc-Gly-OH (35.0 g, 200 mmol) to H-Ala-OCH$_3$.HCl (27.9 g, 200 mmol) using a mixed anhydride procedure. The resulting product (43.5 g, 167 mmol) was deblocked with anhydrous HCl in dioxane. After deblocking, crystallization from dioxane:ether yielded 27.1 g of H-Gly-Ala-OCH$_3$.HCl.

Boc-Phe-OH (26.5 g, 100 mmol) was coupled to H-Gly-Ala-OCH$_3$.HCl (19.6 g, 100 mmol) using a mixed anhydride procedure. After crystallization from ethyl acetate:hexane, 30.2 g of Boc-Phe-Gly-Ala-OCH$_3$ (m.p. 126.4°–127.8°) were obtained.

Anal: Calcd. for $C_{20}H_{29}N_3O_6$: C, 58.95; H, 7.71; N, 10.31; Found: C, 59.49; H, 7.05; N, 10.26.

Boc-Phe-Gly-Ala-OCH$_3$ (28.4 g, 69.7 mmol) was saponified to yield 22 g of solid Boc-Phe-Gly-Ala-OH. It was crystallized from acetone:ether to yield 20 g of product (m.p. 105.7°–109°).

Anal: Calcd. for $C_{19}H_{27}N_3O_6$: C, 58.00; H, 6.92; N, 10.68; Found: C, 58.04; H, 6.78; N, 10.66.

Boc-Phe-Gly-Ala-LeuCH$_2$Cl was prepared by coupling Boc-Phe-Gly-Ala-OH (11.8 g, 30 mmol) to H-LeuCH$_2$Cl.HCl (6.06 g, 30 mmol) using a mixed anhydride procedure. A mixed anhydride of Boc-Phe-Gly-Ala-OH was prepared in a solution of 300 mL of tetrahydrofuran and 25 mL of acetone, and then H-LeuCH$_2$Cl HCl was added in acetone. The resulting crude product, 17.6 g, was dissolved in ether, treated with carbon, and filtered. Product Boc-Phe-Gly-Ala-LeuCH$_2$Cl crystallized from ether (10.0 g).

Anal: Calcd. for $C_{20}H_{39}N_4O_6Cl$: C, 57.93; H, 7.29; N, 10.39; Found: C, 57.92; H, 7.53; N, 10.17.

Boc-Phe-Gly-Ala-LeuCH$_2$Cl (0.30 g) was treated with 1 mL of anhydrous trifluoroacetic acid for 5 minutes at about 23°, forming a trifluoroacetate salt, which was precipitated by addition of cold ether and then washed with additional cold ether. The salt was then dried over solid potassium hydroxide and phosphorus pentoxide to yield 0.31 g (0.55 mmole) of H-Phe-Gly-Ala-LeuCH$_2$Cl.trifluoroacetate. This product was dissolved in 2 mL of 50% dioxane:water, and the resulting solution was cooled to 0°. Sodium bicarbonate (0.09 g, 1.11 mmol) and succinic anhydride (0.066 g, 0.66 mmole) dissolved in 1 mL of dioxane were added. After 1 hour, 0.55 mL of 1.0N hydrochloric acid was added, and the resulting solution was diluted to 10 mL with water and held overnight at 40°. During this period product Suc-Phe-Gly-Ala-LeuCH$_2$Cl crystallized from solution. This product was filtered and washed with 100 mL of cold 0.10N hydrochloric acid. After drying in vacuo, 0.18 g of Suc-Phe-Gly-Ala-LeuCH$_2$Cl (m.p. 157.5°–158°) was obtained.

Anal: Calcd. for $C_{25}H_{35}N_4O_7Cl$: C, 55.70; H, 6.56; N, 10.40; Found: C, 55.47; H, 6.59; N, 10.48.

I. MeOSuc-Phe-Gly-Ala-LeuCH$_2$Cl

Suc-Phe-Gly-Ala-LeuCH$_2$Cl (0.20 g, 0.37 mole) was dissolved in 10 mL of acetone, and the resulting solution was treated with diazomethane:ether (10 mL) for 30 minutes at 0°. Solvent was evaporated after the solution was warmed to about 23°. The remaining residue was dissolved in acetone, and the resulting solution was filtered and concentrated by evaporation of solvent. The concentrate was diluted with ethyl acetate, and this solution was again concentrated by evaporation to remove most of the acetone. A crystalline product separated. This product was isolated and washed with cold ethyl acetate to yield 0.11 g of MeOSuc-Phe-Gly-Ala-LeuCH$_2$Cl (m.p. 128.5°–129.5°).

Anal: Calcd. for $C_{26}H_{37}N_4O_7Cl$: C, 56.45; H, 6.76; N, 10.13; Found: C, 56.26; H, 6.69; N, 10.01.

J. Boc-Gly-Ala-LeuCH$_2$Cl

Boc-Gly-Ala-OH was prepared by an N-hydroxysuccinimide coupling procedure. Boc-Gly-OSu (7.67 g, 28.2 mmol) was dissolved in 10 mL of dimethylsulfoxide, and the resulting solution was added to a solution consisting of H-Ala-OH (3.76 g, 42.3 mmol) and triethylamine (5.89 mL, 42.3 mmol) in 20 mL of water. After stirring overnight, a precipitate was removed by filtration. The remaining solution was diluted with water and then acidified with hydrochloric acid. An aqueous phase separated from which product was extracted by addition of ethyl acetate. The ethyl acetate extract was washed with 0.2N hydrochloric acid and then saturated sodium chloride prepared in 0.2N hydrochloric acid. The washed ethyl acetate solution was then dried over sodium sulfate and filtered. Solvent was then evaporated, leaving a foamy product, which was crystallized from ethyl acetate:hexane to yield 2.88 g of Boc-Gly-Ala-OH (m.p. 128°–130°).

Anal: Calcd. for $C_{10}H_{18}N_2O_5$: C, 48.76; H, 7.38; N, 11.38; Found: C, 49.12; H, 7.27; N, 11.28.

Boc-Gly-Ala-OH (2.5 g, 10.2 mmol) was coupled to H-LeuCH$_2$Cl.HCl by a procedure substantially similar to that described for the preparation of Z-Phe-Gly-Leu-LeuCH$_2$Cl. Evaporation of ethyl acetate provided 3.7 g of a foam. Crystallization from ethyl acetate:hexane gave 3.1 g of Boc-Gly-Ala-LeuCH$_2$Cl (m.p. 95°–99.5°).

Anal: Calcd. for $C_{17}H_{30}N_3O_5Cl$: C, 52.09; H, 7.73; N, 10.72; Found: C, 52.21; H, 7.46; N, 10.63.

K. Z-Phe-Ser-Ala-LeuCH$_2$Cl

Z-Phe-Ser(OCH$_2$C$_6$H$_5$)-Ala-OH was prepared according to the following mixed anhydride coupling procedure.

First, Boc-Ser(OCH$_2$C$_6$H$_5$)-OH (4.93 g, 16.7 mmol) was coupled to H-Ala-OCH$_3$.HCl (2.80 g, 20.0 mmol) by a mixed anhydride procedure to yield an oil, 6.1 g. Boc-Ser(OCH$_2$C$_6$H$_5$)-Ala-OCH$_3$ was then deblocked with trifluoroacetic acid, and the resulting product, H-Ser(OCH$_2$C$_6$H$_5$)-Ala-OCH$_3$.trifluoroacetate (6.15 g, 15.6 mmol), was coupled to Z-Phe-OH (3.89 g, 13.0 mmol) using a mixed anhydride procedure. This product was crystallized from ethyl acetate to yield 5.4 g of Z-Phe-Ser(OCH$_2$C$_6$H$_5$)-Ala-OCH$_3$ (m.p. 158°–159°).

Anal: Calcd. for C$_{31}$H$_{35}$N$_3$O$_7$: C, 66.28; H, 6.29; N, 7.48; Found: C, 65.54; H, 6.24; N, 7.37.

Z-Phe-Ser(OCH$_2$C$_6$H$_5$)-Ala-OCH$_3$ (5.63 g, 8.24 mmol) was saponified substantially as previously described, except that 16 mL of dioxane and 8.25 mL of 1.00N sodium hydroxide were used. The desired product, Z-Phe-Ser(OCH$_2$C$_6$H$_5$)-Ala-OH, crystallized from methanol:ethyl acetate to yield 3.5 g (m.p. 171.5°–172.5°).

Anal: Calcd. for C$_{30}$H$_{33}$N$_3$O$_7$: C, 65.79; H, 6.08; N, 7.67; Found: C, 65.50; H, 5.86; N, 7.84.

Z-Phe-Ser(OCH$_2$C$_6$H$_5$)-Ala-LeuCH$_2$Cl was prepared by coupling Z-Phe-Ser(OCH$_2$C$_6$H$_5$)-Ala-OH (1.37 g, 2.5 mmol) to H-LeuCH$_2$Cl.HCl by a mixed anhydride coupling procedure substantially similar to that used for the preparation of Z-Phe-Gly-Leu-LeuCH$_2$Cl in Procedure C, above. Product was obtained as a crystalline solid, 0.98 g (m.p. 167°–168°). Anal: Calcd. for C$_{37}$H$_{45}$N$_4$O$_7$: C, 64.09; H, 6.56; N, 8.08; Found: C, 64.22; H, 6.38; N, 8.08.

Z-Phe-Ser(OCH$_2$C$_6$H$_5$)-Ala-LeuCH$_2$Cl (0.71 g, 10.2 mmol) was treated with a mixture of 15 mL of anhydrous HF and 1 mL of anisole in a commercial HF apparatus (Peptide Institute, Inc.) After 70 minutes at 0°, HF was removed by evaporation, leaving a residue which was dried in vacuo over potassium hydroxide overnight. H-Phe-Ser-Ala-LeuCH$_2$Cl.HF, 0.35 g, was obtained after triturating the residue with ether.

This hydrofluoride salt (0.39 g, 0.71 mmole) was dissolved in a mixture of 2 mL water and 1 mL of dioxane. The resulting solution was cooled to 0° and carbobenzoxychloride (0.10 mL, 0.71 mmole) and sodium bicarbonate (0.12 g, 1.42 mmol) were added. After 30 minutes at 0°, no ninhydrin positive material could be detected. The resulting reaction mixture was diluted with ethyl acetate and the resulting organic layer was washed sequentially with 5% sodium bicarbonate solution, 0.2N hydrochloric acid, and saturated sodium chloride. The washed solution was dried over sodium sulfate and solvent was evaporated, leaving a residue, which was diluted by 50% with hexane to yield 0.13 g of Z-Phe-Ser-Ala-LeuCH$_2$Cl (m.p. 155°–157°).

Anal: Calcd. for C$_{30}$H$_{39}$N$_4$O$_7$Cl: C, 59.73; H, 6.53; N, 9.29; Found: C, 59.81; H, 6.47; N, 9.13.

L Z-Phe-Gly-Ser-LeuCH$_2$Cl

Z-Phe-Gly-Ser-LeuCH$_2$Cl was prepared by the following procedure. First, Z-Phe-Gly-Ser(OCH$_2$C$_6$H$_5$)LeuCH$_2$Cl (0.98 g, 14.4 mmol) was deblocked by treatment with 15 mL of anhydrous HF and 1 mL of anisole (Procedure K) to yield 0.69 g of H-Phe-Gly-Ser-LeuCH$_2$Cl.HF. This intermediate (0.59 g, 12.4 mmol) was then coupled with carbobenzoxychloride substantially according to the procedure of Procedure K to yield 0.4 g of Z-Phe-Gly-Ser-LeuCH$_2$Cl (m.p. 146°–146.5°) after crystallization from ethyl acetate/hexane.

Anal: Calcd. for C$_{29}$H$_{37}$N$_4$O$_7$Cl: C, 59.12; H, 6.34; N, 9.51; Found: C, 59.45; H, 6.37; N, 9.46.

Biological Activity of Selected Peptide Halomethyl Ketones

Selected compounds useful in the processes of the present invention have been shown to inhibit viral protease activity in two assays. One assay, known as a viral cleavage assay, involves comparison of patterns of protein synthesis (as visualized by incorporation of labeled amino acids) in virus-infected HeLa cells grown in the presence and absence of a selected test compound. A second assay, known as a plaque inhibition assay, involves an assessment of the effects of test compounds upon the infectivity of virus in agar-overlaid cell cultures. Toxic effects of a test compound, if any, will also be observed during the incubation period of the plaque inhibition assay. Both assays are described in greater detail below.

Viral Cleavage Assay

In this assay, samples of growing HeLa-O cells were exposed to human poliomyelitisvirus type 2 or human rhinovirus type 1A at a virus concentration of about 10 infectious virus particles per cell. After several hours, host cell metabolism was markedly inhibited, and added radioactive amino acids were incorporated into viral proteins only. After varying concentrations of a test compound were added to cell samples, viral proteins were labeled for 60 minutes at the mid-cycle of infection (3–5 hours after first exposure of the cells to the virus). Cell samples were then solubilized in 0.01M tris(hydroxymethyl)-aminomethane buffer, pH 6.8, containing 1% (w/v) sodium dodecyl sulfate and 1% (v/v) 2-mercaptoethanol. The resulting labeled viral proteins were separated on a polyacrylamide gel and detected by autoradiography, as previously described by Korant et al., *Proc. Natl. Acad. Sci. USA* 76:2992 (1979). If a selected concentration of the test compound disrupted the usual pattern of virus protein processing, that compound was scored as active at that concentration. Gels corresponding to cell samples labeled in the presence of test compounds exhibiting viral protease-inhibiting activity were generally distinguishable by appearance of high molecular weight protein species not apparent on control gels.

Plaque Inhibition Assay

In this assay, cultured HeLa cells were grown to confluency in 60 mm plastic petri dishes. Each culture was then infected with approximately 300 plaque-forming units of virus. Human rhinovirus type 1A was used in the test reported below. The virus employed in this experiment was allowed to absorb to the cells for 30 minutes at 34.5°.

The compound tested was dissolved in ethanol at a concentration 100 times greater than the highest concentration to be tested. The resulting solution was then diluted 1:100 into a solution of McCoy's medium containing 5% heat-inactivated fetal calf serum and 0.38% agar. Two-fold dilutions were then made into agar medium.

After virus adsorbed to the cells, excess virus was washed away and each culture was overlaid with 5 mL of agar medium containing a pre-selected dilution of the compound to be tested. Controls were overlaid with agar medium only. Each culture was then incubated at 34.5° to allow development of plaques.

A plaque is a roughly circular region of dead cells in a culture, indicating an area where one plaque-forming unit of virus first infected one cell. The agar overlay restricts virus mobility, so that viral infection is communicated only between contiguous cells.

When plaques in control cultures were large enough to be observed, yet still relatively discrete, all cultures were stained with 1% crystal violet. Plaques appeared as clear areas in a deep purple field of uninfected cells. Toxic doses of the test compound resulted in visible cell detachment in culture dishes.

EXAMPLES 1-19 AND COMPARISONS A-J: PROTEASE-INHIBITING ACTIVITY OF PEPTIDE HALOMETHYL KETONES IN VIRAL CLEAVAGE ASSAY

The results obtained in a series of experiments in which representative tetrapeptide and tripeptide chloromethyl ketones were tested for protease-inhibiting activity in the viral cleavage assay using poliovirus are set forth in Tables 1 and 2 below. The results are scored as follows:

TABLE 1

Protease-Inhibiting Activity of Selected Peptide Halomethyl Ketones

| Example | Peptide Analog | Activity |
|---|---|---|
| 1 | Z—Phe—Gly—Ala—LeuCH$_2$Cl | +++ |
| 2 | Ac—Phe—Gly—Ala—LeuCH$_2$Cl | +++ |
| 3 | Suc—Phe—Gly—Ala—LeuCH$_2$Cl | +++ |
| 4 | MeOSuc—Phe—Gly—Ala—LeuCH$_2$Cl | +++ |
| 5 | DNS—Phe—Gly—Ala—LeuCH$_2$Cl | +++ |
| 6 | DNP—Phe—Gly—Ala—LeuCH$_2$Cl | +++ |
| 7 | Boc—Gly—Ala—LeuCH$_2$Cl | ++ |
| 8 | Z—Leu—Gly—Ala—LeuCH$_2$Cl | +++ |
| 9 | Z—Phe—Gly—Gly—LeuCH$_2$Cl | +++ |
| 10 | Z—Phe—Gly—Ala—LeuCH$_2$Br | +++ |
| 11 | Z—Phe—Gly—Ala—ValCH$_2$Cl | ++ |
| 12 | Z—Phe—Gly—Leu—LeuCH$_2$Cl | ++++ |
| 13 | Z—Phe—Leu—Ala—LeuCH$_2$Cl | ++ |
| 14 | Z—Phe—Gly—Phe—LeuCH$_2$Cl | ++ |
| 15 | Z—Phe—Gly—Ser—LeuCH$_2$Cl | ++ |
| 16 | Z—Phe—Gly—Pro—LeuCH$_2$Cl | ++ |
| 17 | MeOSuc—Ala—Ile—Phe—LeuCH$_2$Cl | +++ |
| 18 | MeOSuc—Phe—Gly—Leu—Glu(OCH$_3$)CH$_2$Cl | ++++ |
| 19 | MeOSuc—Ala—Ile—Phe—Glu(OCH$_3$)CH$_2$Cl | +++ |
| 20 | Z—Phe—Gly—Ala—TyrCH$_2$Cl | ++ |

− no activity
+/− low activity
+ active at 100 μg/mL
++ active at 50 μg/mL
+++ active at 10 μg/mL
++++ active at <5 μg/mL

TABLE 2

Comparative Experiments Involving Other Peptide Halomethyl Ketones

| Comparison | Peptide Analog | Activity |
|---|---|---|
| A | H—Phe—Gly—Ala—LeuCH$_2$Cl | +/− |
| B | Z—Ala—Gly—Ala—LeuCH$_2$Cl | +/− |
| C | Z—Gln—Gly—Ala—LeuCH$_2$Cl | + |
| D | Z—Phe—Phe—Ala—LeuCH$_2$Cl | +/− |
| E | Z—Phe—Ser—Ala—LeuCH$_2$Cl | + |
| F | Z—Phe—Gly—Lys—LeuCH$_2$Cl | + |
| G | Z—Phe—Lys—Ala—LeuCH$_2$Cl | + |
| H | Z—Phe—Pro—Ala—LeuCH$_2$Cl | + |
| I | Ac—Phe—Gly—Glu—LeuCH$_2$Cl | +/− |
| J | Ac—Phe—Glu(OEt)—Ala—LeuCH$_2$Cl | +/− |

TABLE 2-continued

Comparative Experiments Involving Other Peptide Halomethyl Ketones

| Comparison | Peptide Analog | Activity |
|---|---|---|
| K | Ac—Phe—Glu—Ala—LeuCH$_2$Cl | +/− |

EXAMPLE 20

The antiviral activity of Z-Phe-Gly-Leu-LeuCH$_2$Cl on rhinovirus type 1A was evaluated by a plaque inhibition assay as described above. Antiviral activity, as scored by 90% plaque reduction, was noted at 1 μg/mL, whereas cytotoxicity was first detected at a concentration of about 15 μg/mL with human HeLa-O cells. 9n

What is claimed is:

1. A process for treating picornavirus infection in a mammal, comprising administering to a mammal an effective antiviral amount of a compound of the formula

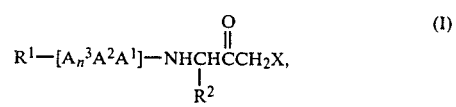

or a physiologically acceptable salt thereof, wherein
  $A^1$ is an amino acid residue selected from the group consisting of Ala, Val, Leu, Ile, Phe, Tyr, Gly, Pro, Ser, and Thr;
  $A^2$ is an amino acid residue selected from the group consisting of Ala, Val, Leu, Ile, and Gly;
  $A^3$ is an amino acid residue selected from the group consisting of Ala, Val, Leu, Ile, Phe, Tyr, and Gly;
  $R^1$ is an N-terminal protecting group; and
  $R^2$ is methyl, isopropyl, isobutyl, 4-hydroxybenzyl, or

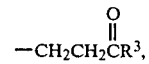

wherein
  $R^3$ is amino, methoxy, ethoxyl, benzyloxy, or alkyl of 1 to 6 carbon atoms;
  X is Cl or Br; and
  n is 0 or 1; with the proviso that both $A^3$ and $A^1$ are not simultaneously Ala.

2. A process according to claim 1, wherein n is 1.

3. A process according to claim 2, wherein $R^1$ is Z, Ac, Boc, MeOSuc, Suc, DNS, or DNP.

4. A process according to claim 3, wherein $R^2$ is isopropyl, isobutyl, or

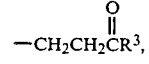

wherein
  $R^3$ is methoxyl.

5. A process according to claim 4, wherein $A^1$ is selected from the group consisting of Ala, Val, Leu, Ile, Phe, Gly, Pro, and Ser.

6. A process according to claim 5, wherein $A^2$ is selected from the group consisting of Ala, Val, Leu, Gly, and Ile.

7. A process according to claim 6, wherein
$A^3$ is selected from the group consisting of Ala, Val, Leu, Ile, and Phe.

8. A process according to claim 7, wherein $R^1$ is Z, MeOSuc or Suc.

9. A process according to claim 8, wherein $R^2$ is isopropyl or isobutyl.

10. A process according to claim 9, wherein $A^1$ is Ala, Phe, Leu, Gly, Pro, or Ser.

11. A process according to claim 10, wherein $A^2$ is Ile, Leu, or Gly.

12. A process according to claim 11, wherein $A^3$ is Ala, Val, Leu, or Phe.

13. A process according to claim 12, wherein $A^1$ is Ala, Leu, or Gly.

14. A process according to claim 13, wherein $A^2$ is Ile or Gly.

15. A process according to claim 14, wherein $A^3$ is Phe, Leu, or Ala.

16. A process according to claim 15, wherein $R^1$ is Z or MeOSuc.

17. A process according to claim 16, wherein $R^2$ is isobutyl.

18. A process according to claim 17, wherein $A^1$ is Ala or Leu.

19. A process according to claim 18, wherein $A^2$ is Gly.

20. A process according to claim 19, wherein $A^3$ is Phe.

21. A process according to claim 20, wherein $A^1$ is Ala; and $R^1$ is Z.

22. A process according to claim 20, wherein $A^1$ is Leu; and $R^1$ is Z.

23. A process according to claim 8, wherein $R^2$ is $$-CH_2CH_2CR^3,\;\overset{O}{\underset{\|}{}}$$

where $R^3$ is methoxyl.

24. A process according to claim 23, wherein
$A^1$ is Ala or Leu;
$A^2$ is Gly;
$A^3$ is Phe or Ala; and
$R^1$ is Z or MeOSuc.

25. A process according to claim 24, wherein
$A^1$ is Leu;
$A^3$ is Phe; and
$R^1$ is MeOSuc.

26. A process for treating poliovirus and rhinovirus infection in a mammal, comprising administering to a mammal an effective antiviral amount of a compound defined in claim 1.

* * * * *